US009307953B2

United States Patent
Lee et al.

(10) Patent No.: US 9,307,953 B2
(45) Date of Patent: Apr. 12, 2016

(54) VECTOR INTERPOLATION DEVICE AND METHOD FOR AN ULTRASONIC WAVE IMAGE

(75) Inventors: Kyoungbo Lee, Seoul (KR); Minyoung Eom, Seoul (KR)

(73) Assignee: ALPINION MEDICAL SYSTEMS CO., LTD. (KR)

( * ) Notice: Subject to any disclaimer, the term of this patent is extended or adjusted under 35 U.S.C. 154(b) by 278 days.

(21) Appl. No.: 14/129,801

(22) PCT Filed: Apr. 13, 2012

(86) PCT No.: PCT/KR2012/002802
§ 371 (c)(1),
(2), (4) Date: Dec. 27, 2013

(87) PCT Pub. No.: WO2013/002480
PCT Pub. Date: Jan. 3, 2013

(65) Prior Publication Data
US 2014/0128737 A1    May 8, 2014

(30) Foreign Application Priority Data

Jun. 28, 2011    (KR) .................. 10-2011-0063069

(51) Int. Cl.
*A61B 8/06*    (2006.01)
*A61B 8/00*    (2006.01)
(Continued)

(52) U.S. Cl.
CPC ............. *A61B 8/4444* (2013.01); *A61B 8/06* (2013.01); *A61B 8/14* (2013.01); *A61B 8/483* (2013.01); *A61B 8/5207* (2013.01);
(Continued)

(58) Field of Classification Search
CPC ............................................. A61B 8/06
See application file for complete search history.

(56) References Cited

U.S. PATENT DOCUMENTS

| 6,077,226 A * | 6/2000 | Washburn ............... A61B 8/06 |
| | | 600/443 |
| 6,618,493 B1 | 9/2003 | Torp et al. |
| 7,758,507 B2 | 7/2010 | Yoshikawa et al. |

(Continued)

FOREIGN PATENT DOCUMENTS

| JP | 2002263105 A | 9/2002 |
| JP | 2007222253 A | 9/2007 |

(Continued)

OTHER PUBLICATIONS

International Search Report for PCT/KR2012/002802 (in English and Korean), mailed Nov. 9, 2012; ISA/KR.

*Primary Examiner* — Peter Luong
(74) *Attorney, Agent, or Firm* — Harness, Dickey & Pierce, P.L.C.

(57) ABSTRACT

An apparatus and method for a vector interpolation of an ultrasound image are provided. The apparatus includes a probe, beam former, demodulator and interpolation processor. The probe converts an electric signal into an ultrasound signal, transmits the ultrasound signal to an object, and converts a reflected ultrasound signal from the object into a reflected electric signal. The beam former forms a receive-focused signal based on the electric signal converted from the reflected ultrasound signal by the probe. The demodulator demodulates the receive-focused signal for forming I data corresponding to in-phase components and Q data corresponding to quadrature-phase components. And the interpolation processor performs a vector interpolation with 1:M weighting (M is a natural number) between different complex-valued signals, based on the I data and the Q data.

10 Claims, 7 Drawing Sheets

(51) Int. Cl.
*A61B 8/08* (2006.01)
*A61B 8/14* (2006.01)
*G01S 15/89* (2006.01)
*G01S 7/52* (2006.01)

(52) U.S. Cl.
CPC ........ *G01S 7/52034* (2013.01); *G01S 15/8979* (2013.01); *A61B 8/461* (2013.01); *A61B 8/488* (2013.01)

(56) References Cited

U.S. PATENT DOCUMENTS

2007/0239014 A1 10/2007 Yoshikawa et al.
2013/0274604 A1 10/2013 Eom

FOREIGN PATENT DOCUMENTS

JP 2007244533 A 9/2007
KR 100742467 B1 7/2007

\* cited by examiner

VECTOR INTERPOLATION DEVICE AND METHOD FOR AN ULTRASONIC WAVE IMAGE

TECHNICAL FIELD

The present disclosure in some embodiments relates to an apparatus and a method for a vector interpolation of an ultrasound image. More particularly, the present disclosure relates to an apparatus and a method for a vector interpolation of an ultrasound image, which can provide a more natural visual image of ultrasound waves by performing a real-time interpolation of I-Q complex-valued signals in the complex signal domain in B-mode and C-mode.

BACKGROUND

The statements in this section merely provide background information related to the present disclosure and may not constitute prior art.

Ultrasound imaging systems have a probe for transmitting an ultrasound wave signal to an object in contact with the probe and receiving a reflected ultrasound wave signal (hereinafter called echo) from the object to form and present an ultrasound image on a display based on the received echo signal. The ultrasound image is mainly represented by a brightness-mode (B-mode) using a reflection coefficient depending on the difference in acoustic impedance between different tissues. Besides the B-mode, the ultrasound image has a C-mode that is a color flow image mode or and a BC-mode which provides both of the B-mode and the C-mode for showing the state of blood flows or movements of the object by using Doppler effect.

Meanwhile, treatment procedures such as an examination, biopsy and surgery require an accurate inspection of a patient's lesion or tissue, which may require ultrasound imaging systems to obtain a multifocal ultrasound image. However, acquiring the multifocal ultrasound image may accompany a significant reduction of the frame rate of the ultrasound image provided by the ultrasound imaging system. With a view to increasing the frame rate, some approach decreases the line density. For example, such approach performs only 64 transmissions even with a 128-element probe instead of normal 128 transmissions. However, this scheme will bring a lowered resolution in spite of the doubled frame rate.

Further, the C-mode contains directionality information of data, and applying a linear interpolation to the directional data incurs an interpolation error associated with the directionality.

DISCLOSURE

Technical Problem

In view of these deficiencies, some embodiments of the present disclosure provide an apparatus and a method for a vector interpolation of an ultrasound image, which can offer a more natural visual image of ultrasound waves by performing a real-time interpolation of I-Q complex-valued signals in the complex signal domain in B-mode and C-mode and can prevent an interpolation error of directionality in the C-mode.

SUMMARY

At least one embodiment of the present disclosure provides an apparatus for a vector interpolation of an ultrasound image, comprising a probe, a beam former, a demodulator and an interpolation processor. The probe is configured to convert an electric signal into an ultrasound signal, transmit the ultrasound signal to an object, and convert a reflected ultrasound signal received from the object into an electric signal. The beam former is configured to form a receive-focused signal based on the electric signal converted from the reflected ultrasound signal by the probe. The demodulator is configured to demodulate the receive-focused signal for forming I data corresponding to in-phase components and Q data corresponding to quadrature-phase components. And the interpolation processor is configured to perform a vector interpolation with 1:M weighting (M is a natural number) between different complex-valued signals, based on the I data and the Q data.

The apparatus further comprises an envelope detector and a log compressor. The envelope detector is configured to perform an envelope detection of a signal by using the complex-valued signals that underwent the vector interpolation performed by the interpolation processor. And the log compressor is configured to perform a log compression on an envelope signal outputted from the envelope detector.

Here, the interpolation processor operates based on Euler's formula to perform the vector interpolation depending on the product of different complex-valued signals.

Another embodiment of the present disclosure provides an apparatus for a vector interpolation of an ultrasound image, comprising an autocorrelator, an interpolation processor and a velocity/variance calculator. The autocorrelator is configured to estimate an average velocity and a signal magnitude associated with blood flow based on an autocorrelation method. The interpolation processor is configured to perform a vector interpolation with 1:M weighting (M is a natural number) between different complex-valued signals, based on a phase of a vector according to the average velocity and the signal magnitude of the blood flow. And the velocity/variance calculator is configured to calculate a velocity and a variance of the blood flow by using the average velocity and the signal magnitude which are vector-interpolated by the interpolation processor.

Here, the interpolation processor may determine the phase ($\theta$) in the range of $-\pi < \theta < \pi$ based on a rotation period.

Yet another embodiment of the present disclosure provides a method for a vector interpolation of an ultrasound image, comprising: converting an electric signal into an ultrasound signal, transmitting the ultrasound signal to an object, and converting a reflected ultrasound signal received from the object into an electric signal; forming a receive-focused signal based on the electric signal converted from the reflected ultrasound signal; demodulating the receive-focused signal to form I data corresponding to in-phase components and Q data corresponding to quadrature-phase components; and performing a vector interpolation with 1:M weighting (M is a natural number) between different complex-valued signals, based on the I data and the Q data.

The method further comprises performing an envelope detection of one or more signals by using the complex-valued signals that underwent the performing of the vector interpolation; and performing a log compression on an envelope signal generated by the envelope detection.

Yet another embodiment of the present disclosure provides a method for a vector interpolation of an ultrasound image, comprises estimating an average velocity and a signal magnitude of blood flow based on an autocorrelation method; performing a vector interpolation with 1:M weighting (M is a natural number) between different complex-valued signals, based on a phase of a vector according to a velocity and a change in the signal magnitude of the blood flow; and calculating velocities and a variance of the complex-valued signals which are vector-interpolated.

Here, the performing of the vector interpolation may determine the phase (θ) in the range of $-\pi < \theta < \pi$ based on a rotation period.

Advantageous Effects

According to some embodiments of the present embodiment, an apparatus and a method for a vector interpolation of an ultrasound image are implemented to provide a more natural visual image of ultrasound waves by performing a real-time interpolation of I-Q complex-valued signals in the complex signal domain based on the phase of a vector according to changes in blood flow and the feedback of the real-time interpolation, and to prevent an interpolation error of directionality in the C-mode.

DETAILED DESCRIPTION

Figure 1:
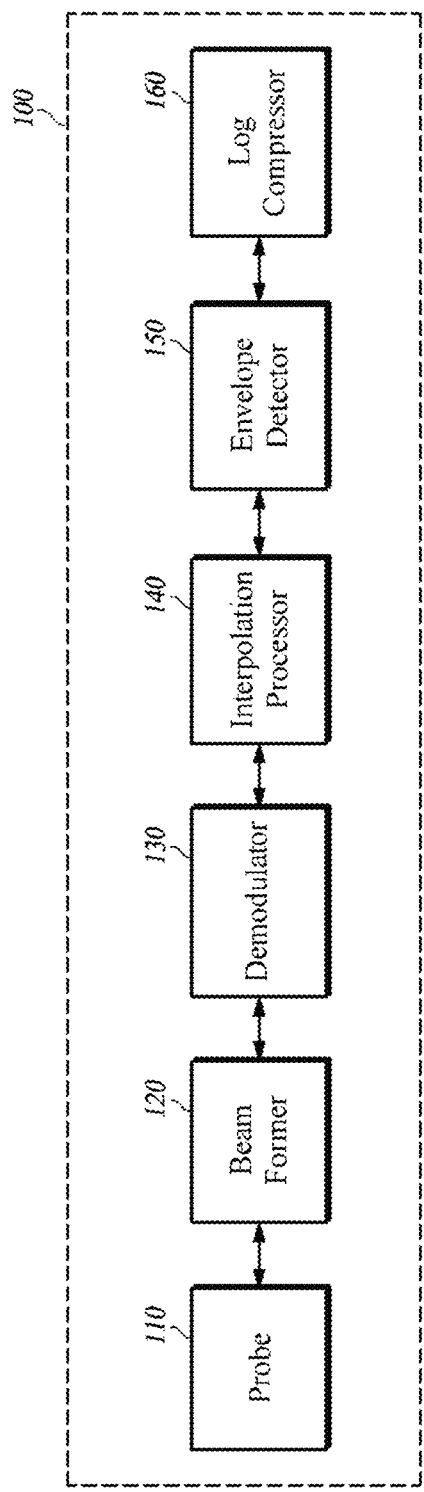
FIG. 1 is a block diagram of an apparatus for a vector interpolation of an ultrasound image according to at least one embodiment.

Hereinafter, some embodiments of the present disclosure will be described in detail with reference to the accompanying drawings. In the following description, like reference numerals designate like elements although the elements are shown in different drawings. Further, in the following description of the at least one embodiment, a detailed description of known functions and configurations incorporated herein will be omitted for the purpose of clarity and for brevity.

Additionally, in describing the components of the present disclosure, terms like first, second, A, B, (a), and (b) are used. These are solely for the purpose of differentiating one component from another, and one of ordinary skill would understand the terms are not to imply or suggest the substances, order or sequence of the components. If a component is described as 'connected', 'coupled', or 'linked' to another component, one of ordinary skill in the art would understand the components are not necessarily directly 'connected', 'coupled', or 'linked' but also are indirectly 'connected', 'coupled', or 'linked' via a third component.

FIG. 1 is a block diagram of an apparatus for a vector interpolation of an ultrasound image according to at least one embodiment.

Referring to FIG. 1, an apparatus 100 for vector interpolation of an ultrasound image according to at least one embodiment includes a probe 110, a beam former 120, a demodulator 130, an interpolation processor 140, an envelope detector 150 and a log compressor 160.

Probe 110 converts an electric signal into an ultrasound signal, transmits the ultrasound signal to an object, and again converts a reflected ultrasound signal into a reflected electric signal. Probe 110 is typically formed by combining a plurality of transducer elements. When the transducer emits the ultrasound signal to the object, an interface, if formed by different acoustic impedances of an acoustic propagation medium, causes reflections and a partial penetration of the ultrasound signal. If the medium has multiple boundaries, they reflect a sequence of echoes back to the transducer with piezo-electric porcelain which is put under stress by the echoes, and thereby generate an electric field proportional to the echo intensity. The generated electric field is finally converted to an electric signal. In this way, an ultrasound pulse emitted to the object develops into multiple pulse echoes back from respective points at different depths (interfaces) within the object. With the round trip distance of the pulse echoes considered, an echo from a tissue located at distance x appears at a position on time axis of $t = 2x/c$ ($c = 1530$ m/s: average speed of sound). Therefore, the reflection position of the echo can be determined based on the delay time of the transmitted pulse.

Beam former 120 forms a receive-focused signal (RF signal) based on the electric signal converted by probe 110. Beam former 120 converts an analog signal generated by each transducer element of the probe 110 into a digital signal and forms a receive-focused signal by adding an appropriate delay to each digital signal in consideration of its time of travel from the object to arrive at each transducer element and then summing all the delayed digital signals.

Demodulator 130 downconverts the receive-focused signal formed by beam former 120 into the baseband signal to form I data corresponding to in-phase components and Q data corresponding to quadrature-phase components. In particular, demodulator 130 passes the receive-focused signal formed by beam former 120 through a high band-pass filter, multiplying the resulting signal by sine and cosine functions before passing the product through a low pass filter and thereby forming the I data and Q data which have been demodulated into the baseband signal.

Based on the I data and Q data formed by demodulator 130, interpolation processor 140 performs a vector interpolation with 1:M weighting between complex-valued signals. Here, M is a natural number. The method for the 1:M weighted vector interpolation will be described with reference to FIGS. 2 and 3.

Envelope detector 150 performs an envelope detection of the signals demodulated by using the signals that underwent the vector interpolation by interpolation processor 140.

Log compressor 160 performs a log compression on the signals that are envelope-detected by envelope detector 150. Subsequent to the log compression, the signals undergo a scan conversion in accordance with applications and geometric characteristics of the transducer before image forming. This log compression outputs the I-Q complex-valued signals to have the dynamic range that is recognizable by human eye since those that underwent the demodulation have the Rayleigh distribution and thus have a very large dynamic range.

Figure 2:
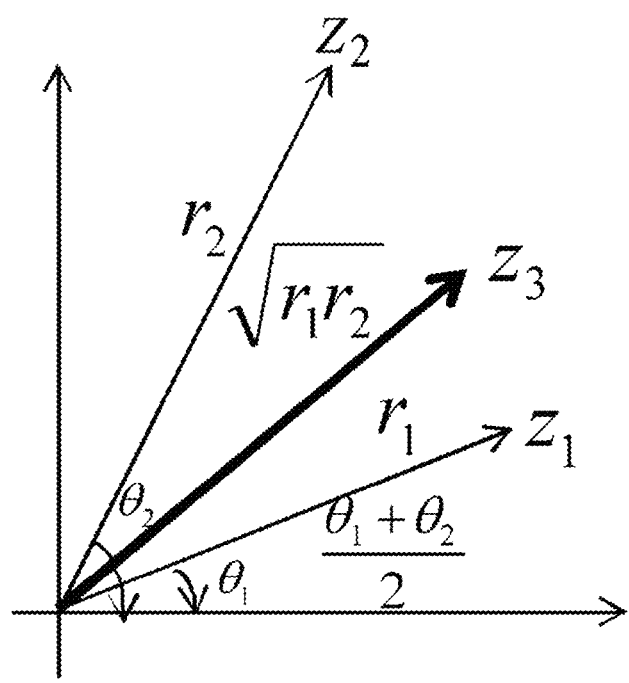
FIG. 2 is an exemplary diagram of a 1:2 vector interpolation between complex-valued signals.

FIG. 2 is an exemplary diagram of a 1:2 vector interpolation between complex-valued signals.

FIG. 2 shows interpolation processor 140 performing a 1:2 weighted vector interpolation on different complex-valued signals $z_1$ and $z_2$ based in the respective data formed by demodulator 130. In this case, interpolation processor 140 may operate based on Euler's formula to perform the vector interpolation depending on the product of the different complex-valued signals.

Assuming the different complex-valued signals $z_1$ and $z_2$ to be $z_1=r_1 e^{j\theta_1}$ and $z_2=r_2 e^{j\theta_2}$ respectively, interpolation processor 140 can perform the 1:2 weighted vector interpolation to calculate interpolated complex-valued signal $z_3$ as shown in Equation 1.

$$I(z_1, z_2) = z_3 = (z_1 z_2)^{1/2} = \sqrt{r_1 r_2}\, e^{j\left(\frac{\theta_1+\theta_2}{2}\right)} \qquad \text{Equation 1}$$

Here, r represents the magnitude of the complex-valued signal, and θ indicates the phase of the complex signal.

Similarly, with respect to different complex-valued signals $z_1$ and $z_2$, interpolation processor 140 may carry out 1:M weighted vector interpolation as in Equation 2.

$$I_{M-1}(z_1, z_2) = z_1^{\frac{1}{M}} z_2^{\frac{M-1}{M}} = r_1^{\frac{1}{M}} r_2^{\frac{M-1}{M}} e^{j\left(\frac{1}{M}\theta_1 + \frac{M-1}{M}\theta_2\right)} \qquad \text{Equation 2}$$

Here, the respective interpolated vectors $l_1(z_1,z_2)$, $l_2(z_1,z_2)$, ..., $l_{M-1}(z_1,z_2)$ of complex-valued signals $z_1$ and $z_2$ may be expressed as Equation 3.

$$I_1(z_1, z_2) = z_1^{\frac{M-1}{M}} z_2^{\frac{1}{M}} = r_1^{\frac{M-1}{M}} r_2^{\frac{1}{M}} e^{j\left(\frac{M-1}{M}\theta_1 + \frac{1}{M}\theta_2\right)}$$

$$I_2(z_1, z_2) = z_1^{\frac{M-2}{M}} z_2^{\frac{2}{M}} = r_1^{\frac{M-2}{M}} r_2^{\frac{2}{M}} e^{j\left(\frac{M-2}{M}\theta_1 + \frac{2}{M}\theta_2\right)}$$

$$I_3(z_1, z_2) = z_1^{\frac{M-3}{M}} z_2^{\frac{3}{M}} = r_1^{\frac{M-3}{M}} r_2^{\frac{3}{M}} e^{j\left(\frac{M-3}{M}\theta_1 + \frac{3}{M}\theta_2\right)}$$

$$\ldots$$

$$I_{M-1}(z_1, z_2) = z_1^{\frac{1}{M}} z_2^{\frac{M-1}{M}} = r_1^{\frac{1}{M}} r_2^{\frac{M-1}{M}} e^{j\left(\frac{1}{M}\theta_1 + \frac{M-1}{M}\theta_2\right)} \qquad \text{Equation 3}$$

Figure 3:
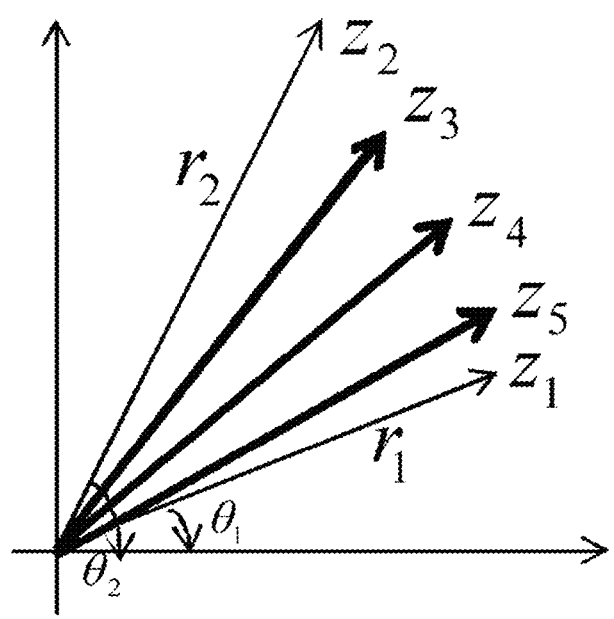
FIG. 3 is an exemplary diagram of 1:M vector interpolation between complex-valued signals.

FIG. 3 is an exemplary diagram of 1:M weighted vector interpolation between complex-valued signals.

As illustrated in the drawing, envelope detector 150 performs an envelope detection on vector-interpolated complex-valued signals and log compressor 160 performs a log compression on the envelope signals.

Figure 4:
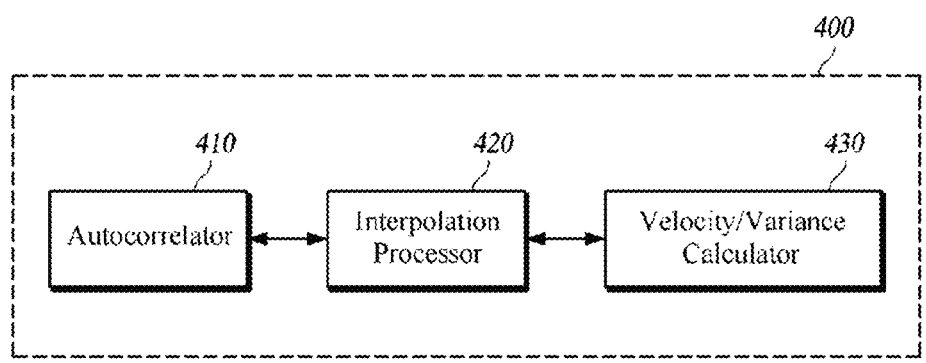
FIG. 4 is a block diagram of an apparatus for a vector interpolation of an ultrasound image according to another embodiment.

FIG. 4 is a schematic diagram of a vector interpolation apparatus for the ultrasound image according to another embodiment of the present disclosure. In this embodiment, the vector interpolation apparatus performs the vector interpolation for C-mode.

Referring to FIG. 4, vector interpolation apparatus 400 of the alternative embodiment includes an autocorrelator 410, an interpolation processor 420 and a velocity/variance calculator 430.

Autocorrelator 410 may estimate the average velocity and the signal magnitude of the blood flow based on the autocorrelation method. The autocorrelation-based Doppler average velocity estimation techniques are known to those skilled in the art and a detailed description thereof will be omitted.

Figure 5:
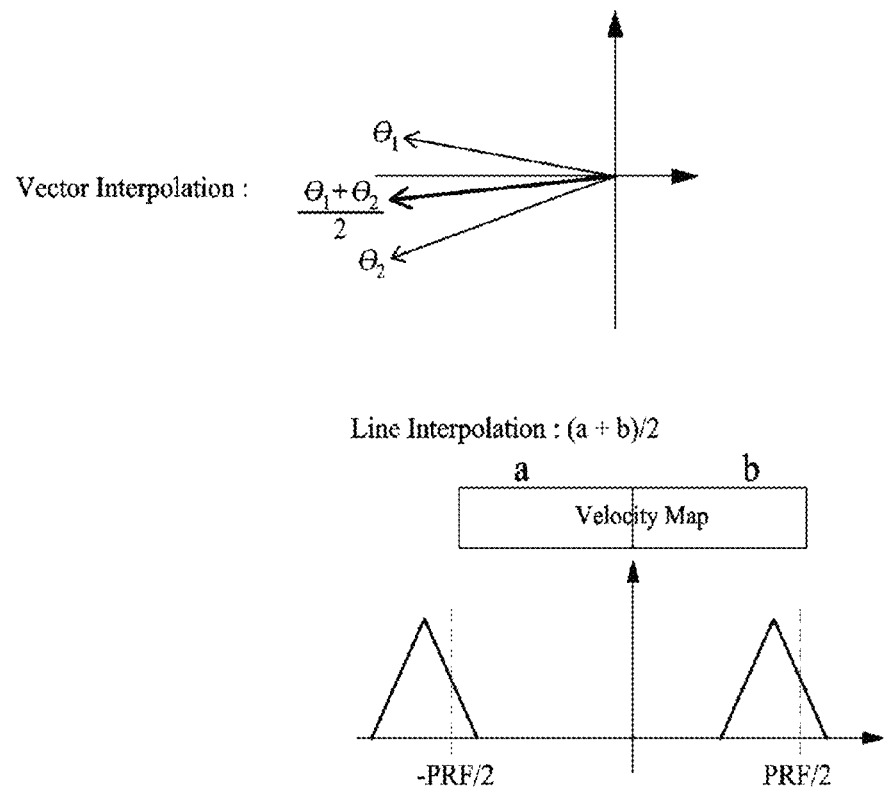
FIG. 5 is an exemplary diagram of interpolations applied to a C-mode image.

Interpolation processor 420 performs a vector interpolation with an 1:M weighting (M represents a natural number) between different complex-valued signals on the basis of the phase of the vector according to the estimated average velocity and signal magnitude of the blood flow from autocorrelator 410. Due to the bidirectivity of information on the blood flow velocity towards and away from the transformer, using linear interpolation may undesirably generate the vector interpolation at the border of two colors a and b, as shown in FIG. 5. Therefore, the interpolation method needs a modification before its application to the C-mode.

To this end, interpolation processor 420 determines the phase (θ) in the range of −π<θ<π based on a rotation period.

For example, assuming the different complex-valued signals to be $z_1^{\theta_0}$ and $z_2^\beta$, vector-interpolated signals $l(z_1, z_2)$ can be expressed as Equation 4.

$$I_1(z_1,z_2)=z_3=z_1^\alpha z_2^\beta = r_1^{\theta_0} r_2^\beta e^{j(\alpha\theta_1+\beta\theta_2)} \qquad \text{Equation 4}$$

Here, $\alpha+\beta=1$.

Here, the sine function of $e^{j(\alpha\theta_1+\beta\theta_2)}$ can be expressed as Equation 5.

$$e^{j(\alpha\theta_1+\beta\theta_2)} = \cos(\alpha\theta_1+\beta\theta_2) + j\sin(\alpha\theta_1+\beta\theta_2) \qquad \text{Equation 5}$$

Figure 6:
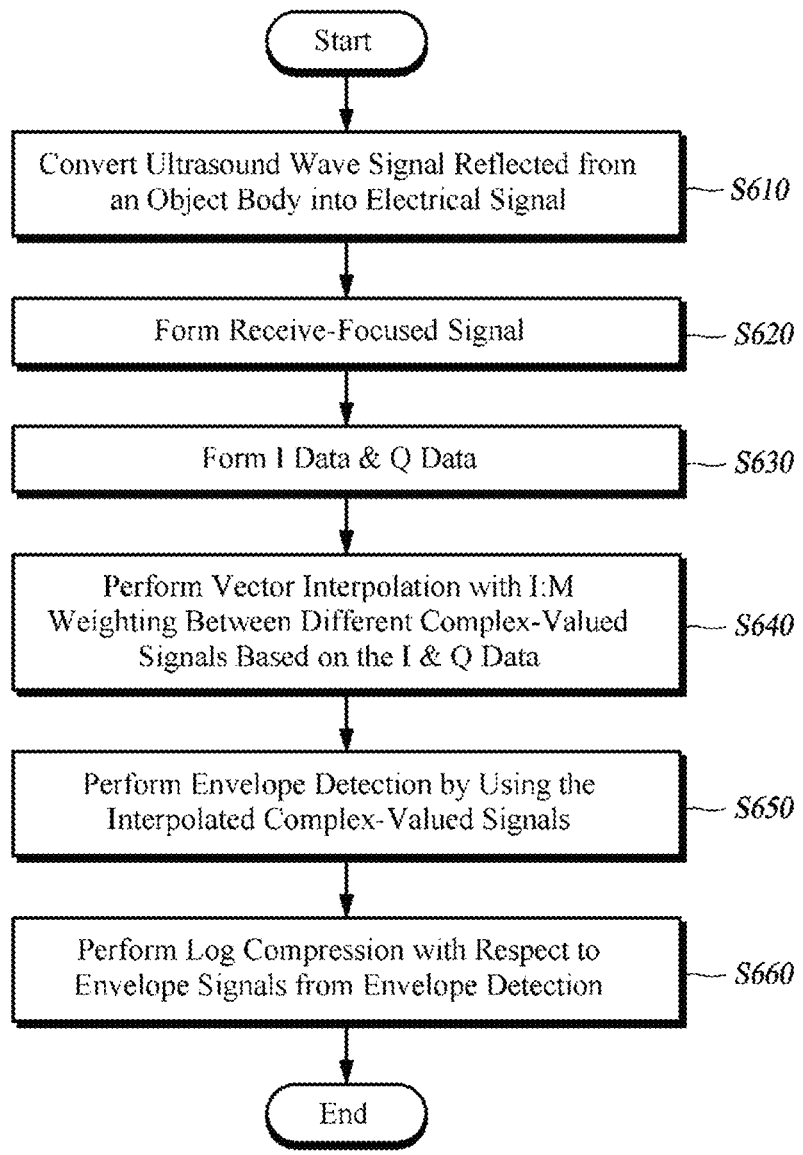
FIG. 6 is a block diagram of a method for a vector interpolation of an ultrasound image according to at least one embodiment.

FIG. 6 is a block diagram of a method for a vector interpolation of an ultrasound image according to at least one embodiment.

Referring to FIGS. 1 to 6, probe 110 converts an electric signal into an ultrasound signal and transmits the ultrasound signal to the object and then converts again a reflected ultrasound signal that has been reflected from the object into a corresponding electric signal at step S610.

Beam former 120 forms an RF (receive-focused) signal based on the electric signal converted by probe 110 (S620). Specifically, beam former 120 converts the analog signal generated by each transducer element of the probe 110 and forms a receive-focused signal by adding an appropriate delay to each digital signal in consideration of its time of travel from the object to arrive at each transducer element and then summing all the delayed digital signals.

Demodulator 130 downconverts the receive-focused signal formed by beam former 120 into the baseband signal to form I data corresponding to in-phase components and Q data corresponding tog quadrature-phase components (S630). Here, demodulator 130 passes the receive-focused signals formed by beam former 120 through a high band-pass filter, multiplies the resulting signal by sine and cosine functions before passing the product through a low pass filter and thereby forms the I data and Q data.

Based on the I data and Q data formed by demodulator 130, interpolation processor 140 performs a vector interpolation with 1:M weighting (M is a natural number) between complex-valued signals (S640).

Envelope detector 150 performs an envelope detection of the signals demodulated by using the vector-interpolated signals from interpolation processor 140 (S650).

Log compressor 160 performs log compression on the signals that are envelope-detected by envelope detector 150 (S660). After the log compression, the signals undergo a scan conversion in accordance with applications and geometric characteristics of the transducer.

Figure 7:
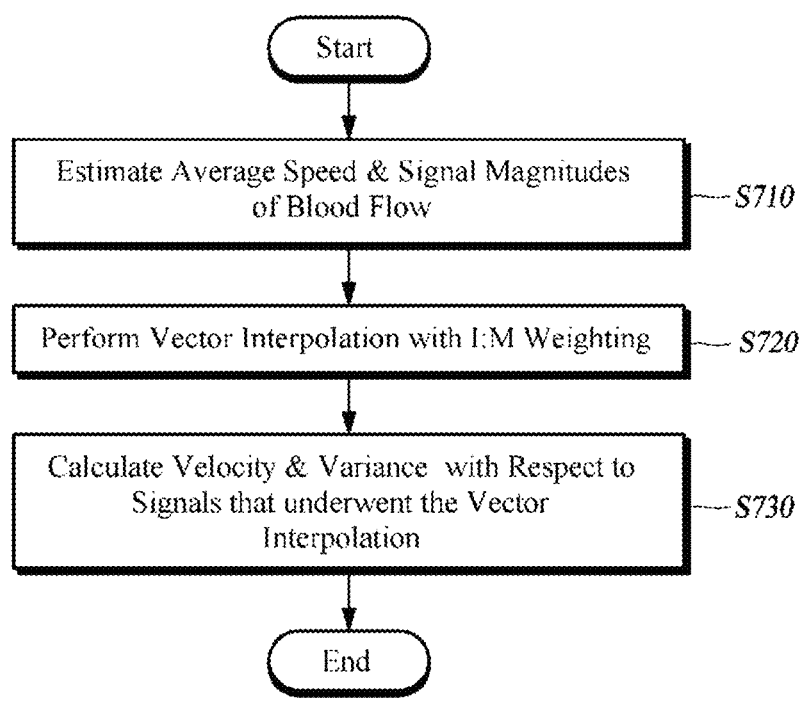
FIG. 7 is a block diagram of a method for a vector interpolation of an ultrasound image according to another embodiment.

FIG. 7 is a block diagram of a method for a vector interpolation of an ultrasound image according to another embodiment.

Referring to FIGS. 4 and 7, autocorrelator 410 may estimate the average velocity and the signal magnitude of the blood flow based on the method for auto-correlation (S710).

Based on the phase of a vector according to the estimated average velocity and signal magnitude from autocorrelator 410, interpolation processor 420 performs a vector interpolation with 1:M weighting (M is a natural number) between different complex-valued signals (S720).

Velocity/variance calculator 430 calculates the velocity and variance of the blood flow with respect to the vector-interpolated signals (S730).

In the description above, although all of the components of the embodiments of the present disclosure may have been explained as assembled or operatively connected as a unit, one of ordinary skill would understand the present disclosure is not limited to such embodiments. Rather, within some embodiments of the present disclosure, the respective components are selectively and operatively combined in any number of ways. Every one of the components are capable of being implemented alone in hardware or combined in part or as a whole and implemented in a computer program having program modules residing in computer readable media and causing a processor or microprocessor to execute functions of the hardware equivalents. Codes or code segments to constitute such a program are understood by a person skilled in the art. The computer program is stored in a non-transitory computer readable media, which in operation realizes the embodiments of the present disclosure. The computer readable media includes magnetic recording media, optical recording media or carrier wave media, in some embodiments.

In addition, one of ordinary skill would understand terms like 'include', 'comprise', and 'have' to be interpreted in default as inclusive or open rather than exclusive or closed unless expressly defined to the contrary. All the terms that are technical, scientific or otherwise agree with the meanings as understood by a person skilled in the art unless defined to the contrary. One of ordinary skill would understand common terms as found in dictionaries are interpreted in the context of the related technical writings not too ideally or impractically unless the present disclosure expressly defines them so.

Although exemplary embodiments of the present disclosure have been described for illustrative purposes, those skilled in the art will appreciate that various modifications, additions and substitutions are possible, without departing from the essential characteristics of the disclosure. Therefore, exemplary embodiments of the present disclosure have been described for the sake of brevity and clarity. Accordingly, one of ordinary skill would understand the scope of the disclosure is not limited by the explicitly described above embodiments but by the claims and equivalents thereof.

CROSS-REFERENCE TO RELATED APPLICATION

If applicable, this application claims priority under 35 U.S.C §119(a) of Patent Application No. 10-2011-0063069, filed on Jun. 28, 2011 in Korea, the entire content of which is incorporated herein by reference. In addition, this non-provisional application claims priority in countries, other than the U.S., with the same reason based on the Korean Patent Application, the entire content of which is hereby incorporated by reference.

The invention claimed is:

1. An apparatus for a vector interpolation of an ultrasound image, the apparatus comprising:
    a probe configured to convert an electric signal into an ultrasound signal, transmit the ultrasound signal to an object, and convert a reflected ultrasound signal received from the object into an electric signal;
    a beam former configured to form a receive-focused signal based on the electric signal converted from the reflected ultrasound signal by the probe;
    a demodulator configured to demodulate the receive-focused signal for forming an I data corresponding to in-phase components and a Q data corresponding to quadrature-phase components; and
    an interpolation processor configured to perform a vector interpolation with 1:M weighting (M is a natural number) between different complex-valued signals, based on the I data and the Q data.

2. The apparatus of claim 1, further comprising:
    an envelope detector configured to perform an envelope detection by using complex-valued signals generated by the vector interpolation; and
    a log compressor configured to perform a log compression on an envelope signal outputted from the envelope detector.

3. The apparatus of claim 1, wherein the interpolation processor performs the vector interpolation by multiplying the different complex-valued signals according to Euler's formula.

4. An apparatus for a vector interpolation of an ultrasound image, the apparatus comprising:
    an autocorrelator configured to estimate an average velocity and a signal magnitude associated with blood flow based on an autocorrelation method;
    an interpolation processor configured to perform a vector interpolation with 1:M weighting (M is a natural number) between different complex-valued signals, based on a phase of a vector according to the average velocity and the signal magnitude of the blood flow; and
    a velocity/variance calculator configured to calculate a velocity and a variance of the blood flow by using the average velocity and the signal magnitude which are vector-interpolated by the interpolation processor.

5. The apparatus of claim 4, wherein the interpolation processor determines the phase ($\theta$) in the range of $-\pi < \theta < \pi$ based on a rotation period.

6. A method for a vector interpolation of an ultrasound image, the method comprising:
    converting an electric signal into an ultrasound signal, transmitting the ultrasound signal to an object, and converting a reflected ultrasound signal received from the object into an electric signal;
    forming a receive-focused signal based on the electric signal converted from the reflected ultrasound signal;
    demodulating the receive-focused signal to form an I data corresponding to in-phase components and a Q data corresponding to quadrature-phase components; and
    performing a vector interpolation with 1:M weighting (M is a natural number) between different complex-valued signals, based on the I data and the Q data.

7. The method of claim 6, further comprising:
    performing an envelope detection by using complex-valued signals generated by the vector interpolation; and
    performing a log compression on an envelope signal generated by the envelope detection.

8. The method of claim 6, wherein the vector interpolation is performed by multiplying the different complex-valued signals according to Euler's formula.

9. A method for a vector interpolation of an ultrasound image, the method comprising:
    estimating an average velocity and a signal magnitude of a blood flow based on an autocorrelation method;
    performing a vector interpolation with 1:M weighting (M is a natural number) between different complex-valued signals, based on a phase of a vector according to a velocity and a change in the signal magnitude of the blood flow; and
    calculating velocities and a variance of the complex-valued signals which are vector-interpolated.

10. The method of claim 9, wherein the performing of the vector interpolation determines the phase ($\theta$) in the range of $-\pi < \theta < \pi$ based on a rotation period.

* * * * *